(12) United States Patent
Tanaka et al.

(10) Patent No.: US 8,004,542 B2
(45) Date of Patent: Aug. 23, 2011

(54) VIDEO COMPOSITION APPARATUS, VIDEO COMPOSITION METHOD AND VIDEO COMPOSITION PROGRAM

(75) Inventors: Shingo Tanaka, Yokohama (JP); Eiji Kamagata, Kamakura (JP); Yoshiyuki Tsuda, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1210 days.

(21) Appl. No.: 11/332,461

(22) Filed: Jan. 17, 2006

(65) Prior Publication Data
US 2006/0170762 A1    Aug. 3, 2006

(30) Foreign Application Priority Data

Jan. 17, 2005 (JP) ................................. 2005-009133

(51) Int. Cl.
G09G 5/00 (2006.01)
G06K 9/32 (2006.01)
(52) U.S. Cl. ..................... 345/660; 382/298
(58) Field of Classification Search .................. 345/619, 345/629, 635, 660, 667, 668; 715/719, 733, 715/751; 348/14.07, 14.09; 382/298
See application file for complete search history.

(56) References Cited

U.S. PATENT DOCUMENTS

| 5,953,050 | A | 9/1999 | Kamata et al. | |
| 6,061,473 | A * | 5/2000 | Chen et al. | 382/235 |
| 7,365,757 | B1 * | 4/2008 | Callway et al. | 345/629 |
| 2002/0145610 | A1 * | 10/2002 | Barilovits et al. | 345/538 |
| 2003/0174146 | A1 * | 9/2003 | Kenoyer | 345/619 |
| 2008/0068446 | A1 * | 3/2008 | Barkley et al. | 348/14.07 |
| 2008/0100696 | A1 * | 5/2008 | Schirdewahn | 348/14.09 |
| 2008/0136899 | A1 * | 6/2008 | Eisenberg et al. | 348/14.09 |

FOREIGN PATENT DOCUMENTS

| JP | 64-064482 | 3/1989 |
| JP | 05-103324 | 4/1993 |
| JP | 09-149396 | 6/1997 |
| JP | 11-088854 | 3/1999 |

OTHER PUBLICATIONS

Office Action dated Jan. 15, 2010 in Japanese Patent Application No. 2006-008942, and English-language translation thereof.
Office Action in Japanese Patent Application No. 2006-008942, dated Mar. 29, 2010, and English-language translation.
Tanaka et al., *Flexibly Layout Controllable Multi-Out Video Mixing Processor*, Proc. of the 2005 IEICE Society Conference, Sep. 2005, 1 page.

* cited by examiner

*Primary Examiner* — Kee M Tung
*Assistant Examiner* — Jacinta Crawford
(74) *Attorney, Agent, or Firm* — Nixon & Vanderhye, P.C.

(57) ABSTRACT

Example video composition systems and methods involve scaling each of multiple input video images with scaling factors to generate a plurality of scaled input video images each corresponding to one of the input video images. The scaled input video images are written into regions in a video storage unit. Video image signals are read out from the video storage unit on the basis of each of multiple video layout information pieces, the video layout information prescribing layout of the input video images when the input video images are composed. A composite video image is generated from the video image signals read out from the video storage unit for every video layout information pieces piece.

17 Claims, 10 Drawing Sheets

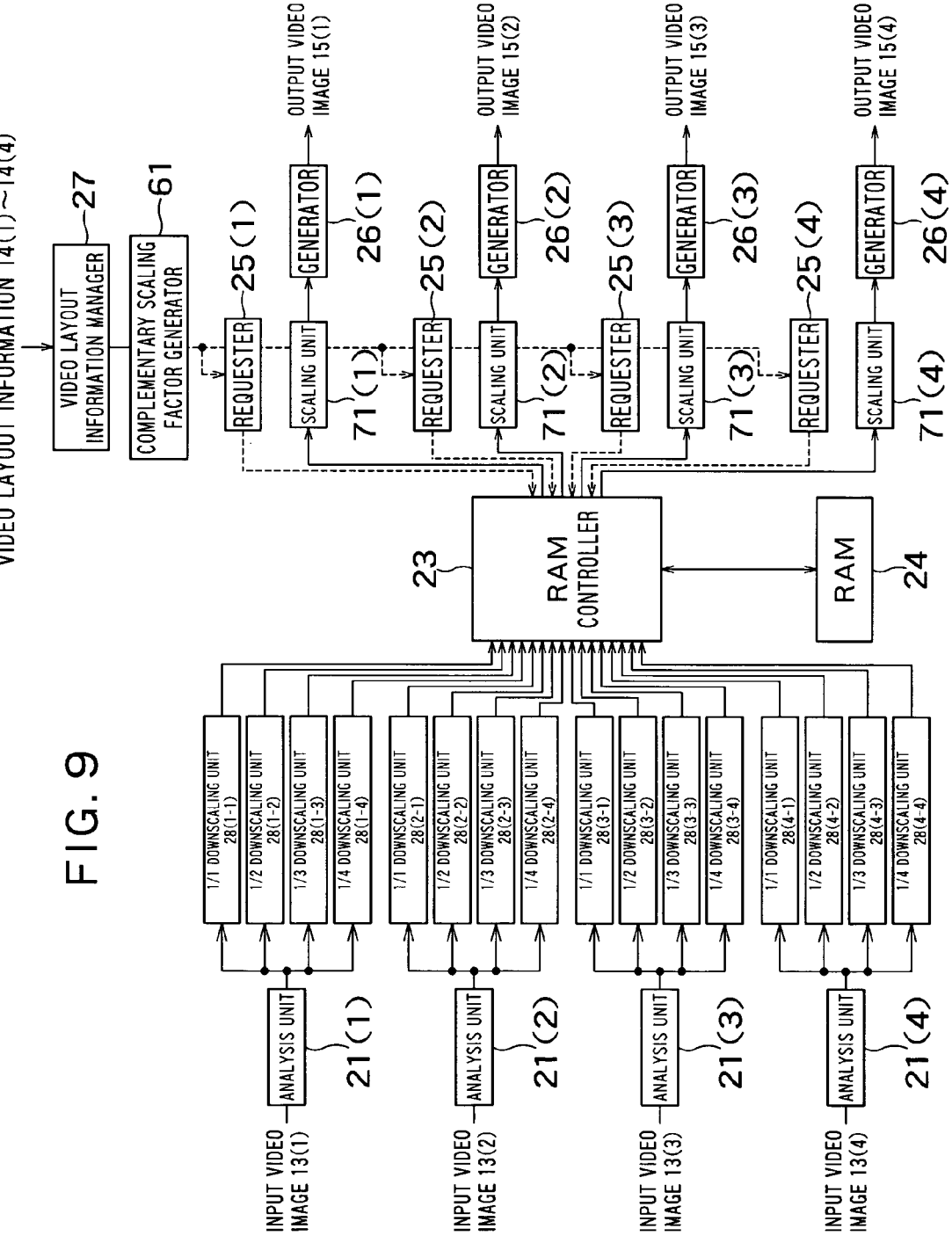

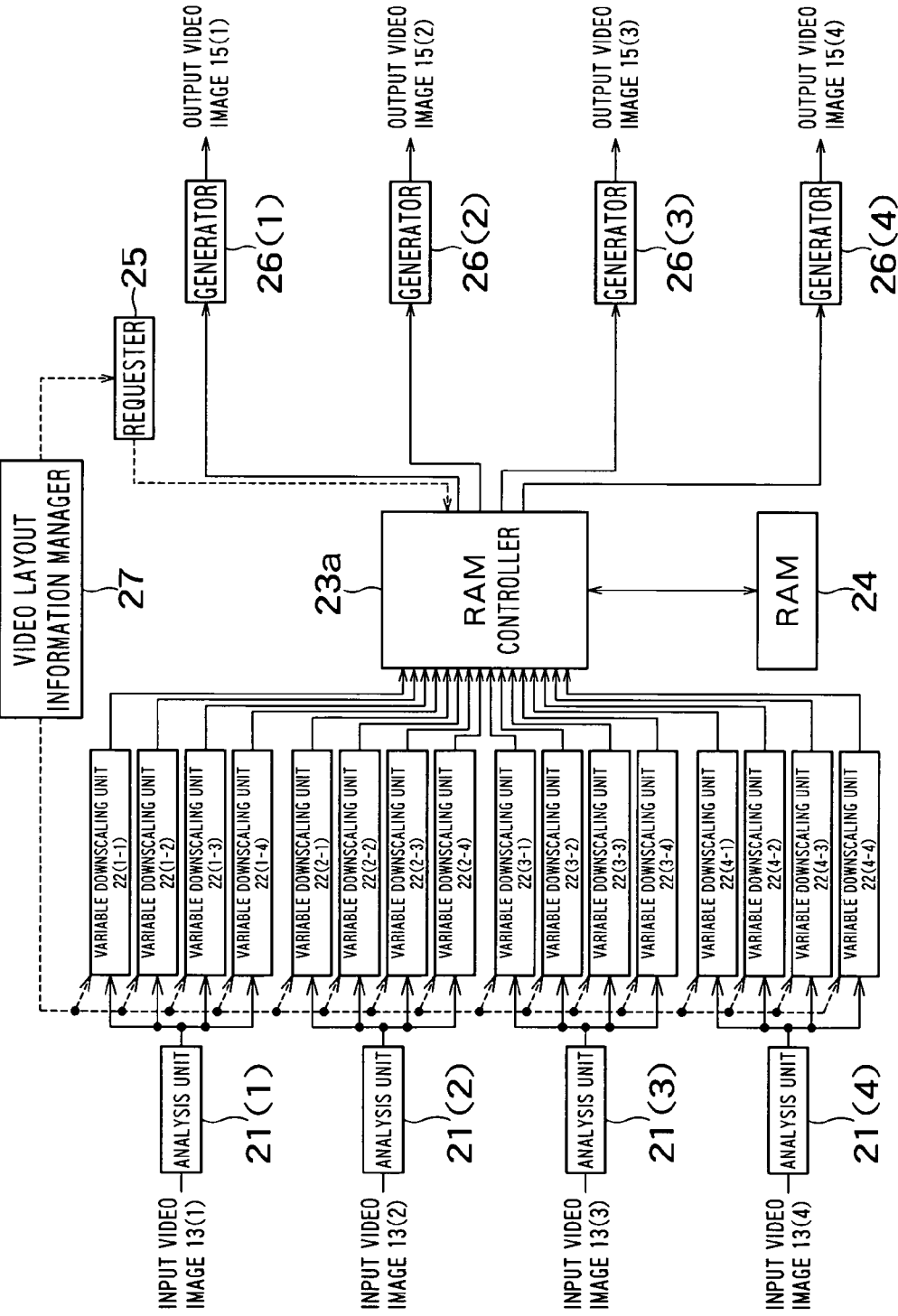

VIDEO COMPOSITION APPARATUS, VIDEO COMPOSITION METHOD AND VIDEO COMPOSITION PROGRAM

CROSS-REFERENCE TO RELATED APPLICATIONS

This application claims the benefit of priority under 35USC §119 to Japanese Patent Application No. 2005-9133 filed on Jan. 17, 2005, the entire contents of which are incorporated herein by reference.

BACKGROUND OF THE INVENTION

1. Field of the Invention

The present invention relates to a video composition apparatus, a video composition method and a video composition program, used to receive a plurality of video signals and output a plurality of video signals obtained by composing those received video signals in different patterns.

2. Description of the Background

In the case of the so-called multipoint video conference in which communication is conducted among a plurality of terminals by using microphone voices and camera video images, the load is heavy in the aspect of communication and terminal processing if simply the terminals are connected in a full mesh form. In general, therefore, a technique of providing an MCU (Multipoint Conference Unit) is used. The MCU is a kind of a server, and has a function of connecting with terminals, receiving voice and video images from the terminals, composing them, and transmitting resultant composite video images and voices to the terminals. Owing to this MCU, it becomes possible for the terminals to obtain voices and video images from all participants by only communicating with the MCU and receiving a composite voice and a composite video image, resulting in a high efficiency in the aspect of communication and terminal processing. In this way, the MCU plays an important role in the multipoint video conference, and a video composition technique is utilized.

As another application of the video composition technique, there is a screen splitting unit in a surveillance camera. In general, a plurality of surveillance camera are installed in a building or the like. If they are observed and recorded using separate monitors, the equipment becomes large-scaled, resulting in lowered convenience. In a typically used technique, therefore, a screen splitting unit is used, and a plurality of camera video images are composed to generate one video signal. The one video signal is viewed using a single monitor or recorded using a single video recorder.

However, most of conventional video composition techniques output a single composite video image. Few conventional techniques propose to output a plurality of composite video images.

For example, the case of the video conference will now be considered. Even in a model in which a composite video image of one kind is generated and all participants watch it as in the conventional technique, the video conference can be implemented. In pursuing greater convenience, however, for example, a demand that a specific video image selected from among a plurality of composite video images should be zoomed and displayed is also made. One solution thereto is described in Japanese Patent Application Laid-Open Publication No. 11-88854. When a certain video image is zoomed, however, video images other than the zoomed video image cannot be watched according to the technique described in Japanese Patent Application Laid-Open Publication No. 11-88854. If the way of composition is changed and, for example, a composite video image obtained by embedding other downscaled images in a zoomed video image can be exhibited, it is more convenient to use. Or if it is possible to exhibit a composite video image obtained by zooming a video image to relatively some degree instead of zooming the video image to the whole screen and displaying other downscaled participants around the zoomed video image, it is more convenient to use. In this case, it is considered that the case where participants desire to zoom in different video images will naturally take place. Therefore, it is demanded to compose video images in different patterns for respective terminals and output a plurality of different composite video images.

A model in which a plurality of composite video images are output is described only in Japanese Patent Application Laid-Open Publication No. 5-103324 so far as we know. In Japanese Patent Application Laid-Open Publication No. 5-103324, a downscaling circuit downscales input video images stored in a video memory, and a composition circuit composes the downscaled video images and outputs resultant composite video images. If it is supposed that this model is actually mounted, however, there is a problem that the circuit becomes complicated. Specifically, the following problems occur.

First, the composition circuit which outputs composed video signals must typically output signals at timing based on standards for output signals. Therefore, input signals must be input to the composition circuit at timing that causes the output timing to satisfy the standards with the processing delay in the composition circuit itself taken into consideration. (If a buffer is provided between the input signals and the composition circuit, the input signals must be input within allowed timing.) On the other hand, in order for the composition circuit to output signals at the above-described timing, a downscaling circuit which generates the input signals to the composition circuit, must read data from a video memory at adapted timing with the processing delay in the downscaling circuit itself taken into consideration. In this way, according to the final output timing of signals from the composition circuit, it is necessary to determine output timing of the downscaling circuit with the processing delay in the composition circuit taken into consideration, and determine timing for reading out data from the video memory with the processing delay in the downscaling circuit taken into consideration.

If in the above-described configuration the composition circuit is formed to be able to dynamically change the composition pattern and the downscaling circuit is formed to be able to dynamically change downscaling factors, delay timing also dynamically changes. As a result, processing which copes with the delays does not become simple, resulting in a complicated circuit and an increased circuit scale.

SUMMARY OF THE INVENTION

According to an aspect of the present invention, there is provided with a video composition apparatus comprising: I video scaling units each of which is configured to scale input video image with scaling factors to generate scaled input video images; a video storage unit configured to store the scaled input video images; write requesters, provided so as to be respectively associated with the video scaling units, each of which is configured to generate a write request to request the video storage unit to write the scaled input video images generated by the video scaling unit into predetermined regions in the video storage unit; one or more read requesters configured to issue read requests of scaled input video images in the video storage unit on the basis of each of J video layout information pieces each of which prescribes layout of the scaled input video images on each of composite video images; a read controller configured to read out scaled input video images from the video storage unit in response to the read requests; and J composite video image generators, provided so as to be respectively associated with the J video layout information pieces, each of which is configured to generate one of the composite video images from the scaled video images read out by the read controller correspondingly to the video layout information piece.

According to an aspect of the present invention, there is provided with a video composition method comprising: scaling each of I input video images with a plurality of scaling factors to generate a plurality of scaled input video images every input video image; writing the scaled input video images generated every input video image into predetermined regions in a video storage unit; reading out video image signals from the video storage unit on the basis of each of J video layout information pieces, the video layout information prescribing layout of the input video images when the input video images are composed; and generating a composite video image from the video image signals read out from the video storage unit every video layout information pieces.

According to an aspect of the present invention, there is provided with a video composition program for inducing a computer to execute: scaling each of I input video images with a plurality of scaling factors to generate a plurality of scaled input video images every input video image; writing the scaled input video images generated every input video image into predetermined regions in a video storage unit; reading out video image signals from the video storage unit on the basis of each of J video layout information pieces, the video layout information prescribing layout of the input video images when the input video images are composed; and generating a composite video image from the video image signals read out from the video storage unit every video layout information pieces.

BRIEF DESCRIPTION OF THE DRAWINGS

FIG. 9 is a block diagram schematically showing a configuration of a video composition apparatus according to a fifth embodiment of the present invention; and FIG. 10 is a block diagram schematically showing a another configuration of a video composition apparatus according to a first embodiment of the present invention.

DESCRIPTION OF THE EMBODIMENTS

First Embodiment

Figure 1:
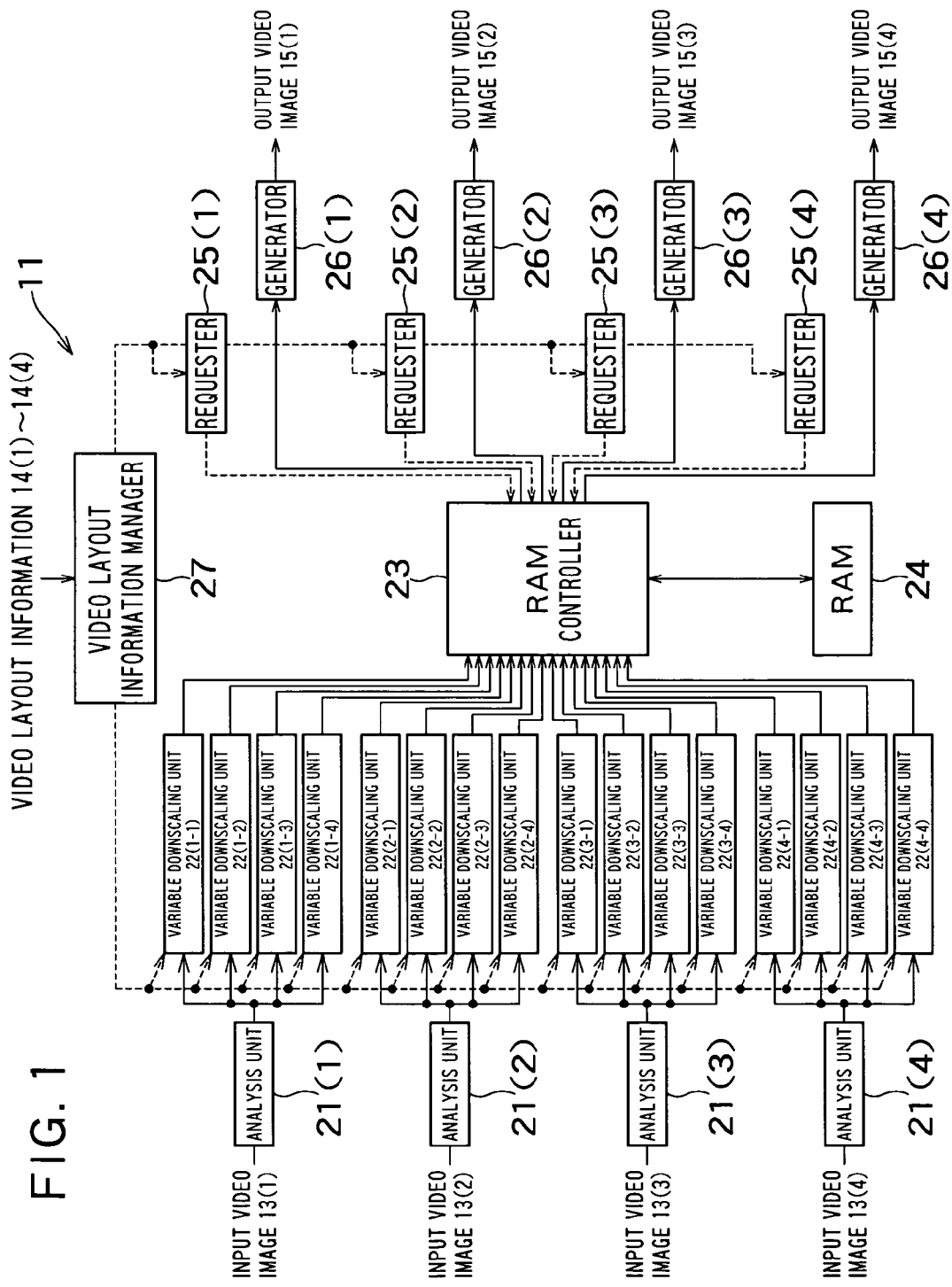
FIG. 1 is a block diagram schematically showing a configuration of a video composition apparatus according to a first embodiment of the present invention.
Figure 2:
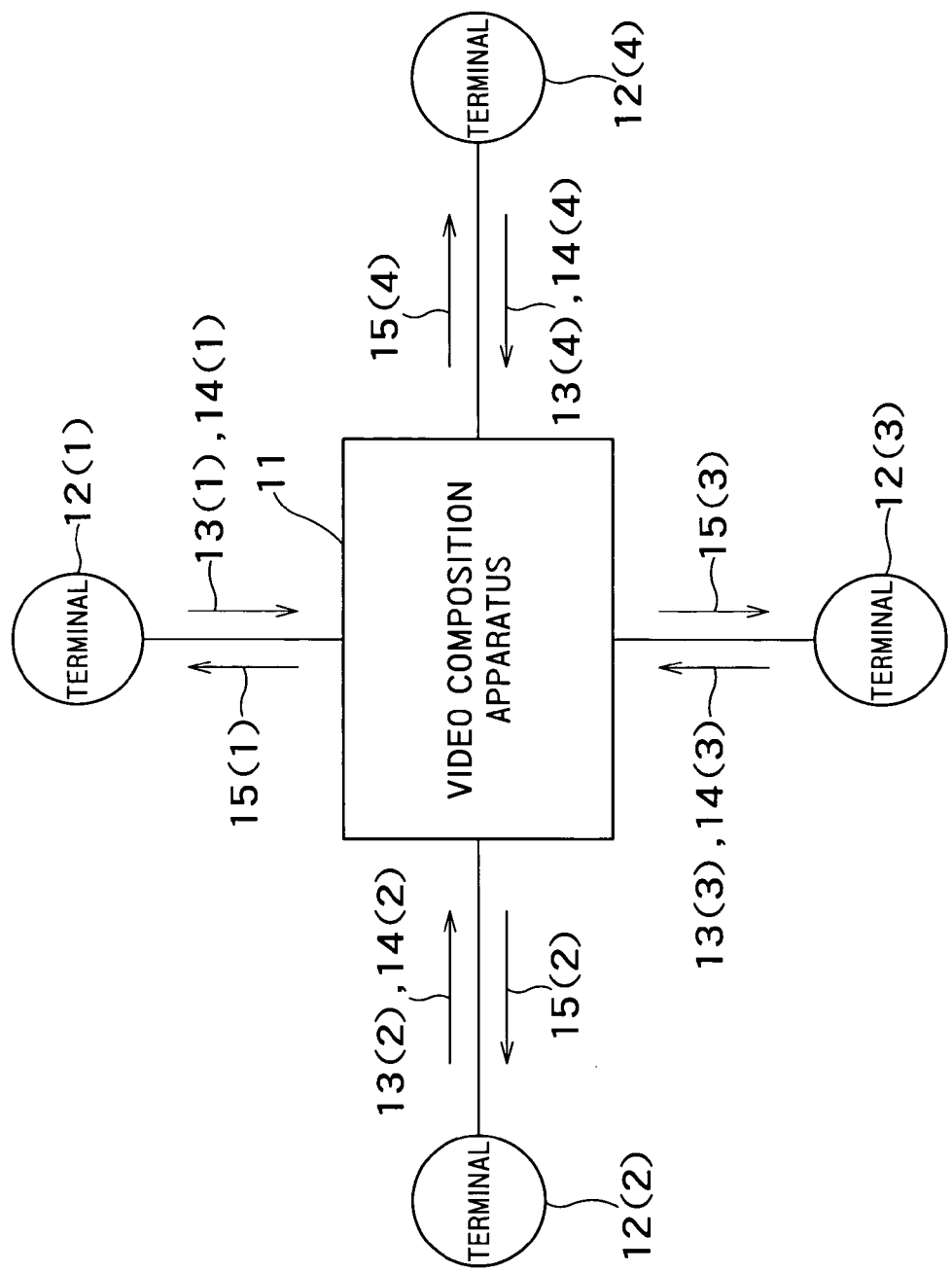
FIG. 2 is a block diagram schematically showing a configuration of a video conference system to which the video composition apparatus shown in FIG. 1 is applied.

FIG. 1 is a block diagram schematically showing a configuration of a video composition apparatus according to a first embodiment of the present invention. FIG. 2 is a block diagram schematically showing a configuration of a video conference system to which the video composition apparatus shown in FIG. 1 is applied.

In FIG. 2, terminals 12(1) to 12(4) are connected to a video composition apparatus 11 via networks which are not illustrated. The terminals 12(1) to 12(4) generate video signals (input video images) 13(1) to 13(4), and transmit them to the video composition apparatus 11. Furthermore, the terminals 12(1) to 12(4) transmit video layout information 14(1) to 14(4) to be used for video composition in the video composition apparatus 11 to the video composition apparatus 11. Each time the layout is changed, the terminals 12(1) to 12(4) newly generate the video layout information and transmit them to the video composition apparatus 11. The video composition apparatus 11 composes video signals 13(1) to 13(4) on the basis of the video layout information 14(1) to 14(4), generates composite video images for the terminals 12(1) to 12(4), and transmits composite video signals (output video images) 15(1) to 15(4) to the terminals 12(1) to 12(4), respectively. In other words, four video signals are input to the video composition apparatus 11, and the video composition apparatus 11 generates and outputs four composite video signals by composing the four video signals. The video signals are transmitted as digital signals according to, for example, specifications in ITU-R (International Telecommunication Union-Radiocommunication) BT.656, and the video signals contain pixel value information. In order to synchronize video frames, synchronization codes are inserted in the video signals at predetermined timing. The synchronization code is a set of FF, 00, 00, and XX. A code indicating the position on the frame is put in XX.

By the way, as a matter of fact, compression transmission may be conducted using MPEG decoders and encoders, which are not illustrated, at the time of transmission of video signals. In other words, an apparatus which transmits a video image first encodes a video signal to an MPEG stream, and an apparatus which receives the MPEG stream decodes the MPEG stream and restores the video signal. According to the foregoing description, it is supposed in this case that the input video signals supplied from the terminals and decoded by the video composition apparatus and the output video signals encoded by the video composition apparatus and supplied to the terminals are based on, for example, BT.656 specifications.

In FIG. 1, the video composition apparatus 11 includes analysis units 21(1) to 21(4), variable downscaling units 22(1-1) to 22(1-4), 22(2-1) to 22(2-4), 22(3-1) to 22(3-4) and 22(4-1) to 22(4-4), a RAM controller 23, a RAM 24, REQUESTERs 25(1) to 25(4), generators 26(1) to 26(4), and a video layout information manager 27. The variable downscaling units in this embodiment have a function as a write requester respectively. The video layout information manager 27 in this embodiment has a function as a scale designation unit.

The analysis units 21(1) to 21(4) analyze synchronization codes included in video signals 13(1) to 13(4) input to them, and find coordinates of current pixel data on the input video image.

The video layout information manager 27 manages layouts of composite video images respectively for the terminals 12(1) to 12(4) on the basis of the video layout information 14(1) to 14(4). The video layout information manager 27 calculates scaling factors (downscaling factors in the present example) respectively for the input video images 13(1) to 13(4) on the basis of the video layout information 14(1) to 14(4), and notifies the variable downscaling units 22(1-1) to 22(1-4), 22(2-1) to 22(2-4), 22(3-1) to 22(3-4) and 22(4-1) to 22(4-4) of the calculated downscaling factors. Each time the video layout information is updated, the video layout information manager 27 calculates the downscaling factors respectively for the input video images 13(1) to 13(4) on the basis of the updated video layout information, and notifies the variable downscaling units of the calculated downscaling factors.

The variable downscaling units 22(1-1) to 22(1-4), 22(2-1) to 22(2-4), 22(3-1) to 22(3-4) and 22(4-1) to 22(4-4) are configured so as to be able to downscale the input video images respectively with a plurality of downscaling factors. The variable downscaling units 22(1-1) to 22(1-4), 22(2-1) to 22(2-4), 22(3-1) to 22(3-4) and 22(4-1) to 22(4-4) downscale the input video images 13(1) to 13(4) on the basis of the downscaling factors specified by the video layout information manager 27.

For example, the variable downscaling units 22(1-1), 22(1-2), 22(1-3) and 22(1-4) downscale the input video images 13(1) disposed on the output video images 15(1) to 15(4) according to the downscaling factors specified by the video layout information manager 27. Furthermore, the variable downscaling units 22(1-1), 22(2-1), 22(3-1), 22(1-4) downscale the input video images 13(1) to 13(4) disposed on the output video image 15(1) according to the downscaling factors specified by the video layout information manager 27.

The variable downscaling units 22(1-1) to 22(1-4), 22(2-1) to 22(2-4), 22(3-1) to 22(3-4) and 22(4-1) to 22(4-4) downscale input video images 13(1) to 13(4) on the basis of coordinate information analyzed by the analysis units 21(1) to 21(4), and request the RAM controller 23 to write the downscaled video images (pixel value information) into predetermined regions (frame buffers for the variable downscaling units) in the RAM 24. The variable downscaling units correspond to, for example, video scaling units.

The RAM controller 23 controls writing into the RAM 24 which stores video signals and reading from the RAM 24. The RAM controller 23 writes pixel value information received from the variable downscaling units 22(1-1) to 22(1-4), 22(2-1) to 22(2-4), 22(3-1) to 22(3-4) and 22(4-1) to 22(4-4) into regions in the RAM 24 specified by the variable downscaling units, reads out pixel value information from the RAM 24 on the basis of read requests from requesters 25(1) to 25(4), and outputs the pixel value information to generators 26(1) to 26(4). The RAM controller corresponds to, for example, a write requester and a read controller.

Each of the generators 26(1) to 26(4) generates a composite video signal obtained by composing the video signals 13(1) to 13(4) on the basis of pixel value information received from the RAM controller 23, and outputs the generated composite video signal while suitably inserting synchronization signals and blanks. At the same time, the generators 26(1) to 26(4) manage coordinates in video frames of composite video signals which are currently being output, and notify the requesters 25(1) to 25(4) of coordinate information to be subsequently read, on the basis of the composite video signals which are currently being output.

The requesters 25(1) to 25(4) issue a read request of pixel value information to be subsequently read, to the RAM controller 23 by referring to the video layout information in the video layout information manager 27 on the basis of coordinate information supplied from the generators 26(1) to 26(4).

The RAM controller 23 reads out requested pixel value information from the RAM 24, and delivers the pixel value information to the generators 26(1) to 26(4).

The RAM 24 has frame buffers associated with the variable downscaling units 22(1-1) to 22(1-4), 22(2-1) to 22(2-4), 22(3-1) to 22(3-4) and 22(4-1) to 22(4-4). In other words, the RAM 24 has a total 4×4=16 frame buffers associated with these variable downscaling units. Pixel value information is written into each frame buffer in order beginning with, for example, its head address. Each time the frame of the input video image is changed, overwriting is conducted again from the head address. By the way, if the so-called double buffer structure is adopted, the capacity of each frame buffer is doubled.

When the RAM controller receives many requests at a same time, there is a time lag between the request and execution in some cases. Therefore, buffers which temporarily hold data may be provided between the variable downscaling units and the RAM controller, and/or between the RAM controller and the generators.

Hereafter, a flow of detailed processing conducted by the video composition apparatus will be described.

In the input system shown on the left side of FIG. 1, 8-bit parallel pixel value information is input to each of the analysis units 21(1) to 21(4) as a video signal according to a 27-MHz clock, in order beginning with a top leftmost pixel on the screen and ending with a bottom rightmost pixel on the screen. In each of a start position and an end position of each line in each frame, a predetermined synchronization code is inserted into the video signal. In addition, in a start position of each frame, a synchronization code indicating the start of the frame is inserted into the video signal.

Each of the analysis units 21(1) to 21(4) manages X coordinate values (for example, 0 to 1715 (inclusive of horizontal blanks)) and Y coordinate values (for example, 0 to 524 (inclusive of vertical blanks)) therein. Each time pixel data arrives, each of the analysis units 21(1) to 21(4) increases the X coordinate value by one. If the X coordinate value arrives at its maximum value, each of the analysis units 21(1) to 21(4) counts from zero again and increases the Y coordinate value by one. If one of the above-described synchronization codes is detected and the synchronization code indicates a start position of a frame, each of the analysis units 21(1) to 21(4) resets the X coordinate values and the Y coordinate values managed therein.

If the current coordinate position is in a blank region at the time of 1/1 downscaling, the pixel value information is invalid. Therefore, each of the variable downscaling units 22(1-1) to 22(1-4), 22(2-1) to 22(2-4), 22(3-1) to 22(3-4) and 22(4-1) to 22(4-4) discards the pixel value information. If the current coordinate position is not in a blank region, the variable downscaling unit delivers the pixel value information as it is to the RAM controller 23. In addition, the variable downscaling unit specifies an address in a frame buffer for 1/1 downscaling associated with coordinates of the pixel value information, as an address to which the pixel value information should be written. If the current coordinate position is not in a blank region at the time of 1/2 downscaling, the variable downscaling unit delivers information obtained by suitably conducting averaging on pixel value information and downscaling an input video image to half in the vertical direction and horizontal direction, to the RAM controller 23. In the same way as the foregoing description, the variable downscaling unit delivers the address to be written as well to the RAM controller 23. In the case of other downscaling factors as well, the variable downscaling unit delivers information to the RAM controller 23 while suitably downscaling the input video images.

Figure 3:
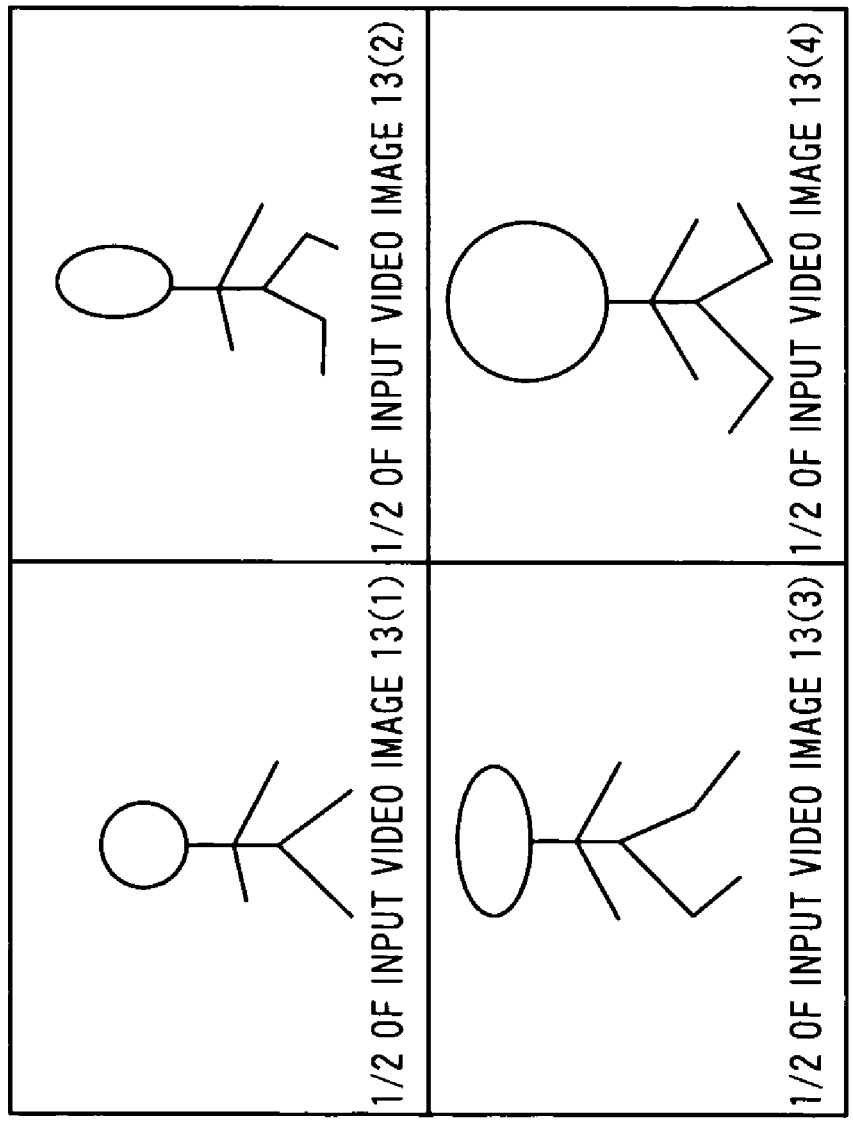
FIG. 3 is a diagram showing an example of a video layout.

For example, if the output video image 15(1) is requested to have a video layout as shown in FIG. 3, the input video image 13(1) is downscaled to 1/2. Therefore, the variable downscaling unit 22(1-1) executes 1/2 downscaling. The RAM controller 23 writes pixel value information suitably received from the variable downscaling unit 22(1-1) into an address in the RAM 24 specified by the variable downscaling unit 22(1-1). The foregoing description holds true of other input video images 13(2) to 13(4) as well.

On the other hand, in the output system shown on the right side of FIG. 1, each of the generators 26(1) to 26(4) manages the X coordinate value and the Y coordinate value, and updates the value one by one according to a 27 MHz clock in the same way as the analysis units 21(1) to 21(4), in order to generate a BT.656 signal in the same way as the input system.

If the above-described video layout shown in FIG. 3 is requested, the requester 25(1) specifies a coordinate address in an input video image on the basis of a coordinate value specified by the generator 26(1) and sends the coordinate address to the RAM controller 23. If the coordinate value specified by the generator 26(1) indicates an upper left-hand position in the video layout, the requester 25(1) specifies a coordinate address in the input video image 13(1) downscaled to 1/2. If the coordinate value specified by the generator 26(1) indicates an upper right-hand position in the video layout, the requester 25(1) specifies a coordinate address in the input video image 13(2) downscaled to 1/2. If the coordinate value specified by the generator 26(1) indicates a lower left-hand position in the video layout, the requester 25(1) specifies a coordinate address in the input video image 13(3) downscaled to 1/2. If the coordinate value specified by the generator 26(1) indicates a lower right-hand position in the video layout, the requester 25(1) specifies a coordinate address in the input video image 13(4) downscaled to 1/2. The RAM controller 23 reads pixel value information from an address in the RAM 24 specified by the requester 25(1), and delivers the pixel value information thus read to the generator 26(1).

Each of the generators 26(1) to 26(4) outputs the received pixel value information as an ITU-R BT.656 signal according to a 27-MHz clock while suitably inserting blanks and synchronization codes therein.

According to the present embodiment, it becomes possible to compose four input video images in four patterns and generate and output four composite video images, as heretofore described.

Furthermore, each variable downscaling unit conducts processing in synchronism with the associated input video image, and each requester conducts processing in synchronism with the associated output video image. In other words, the variable downscaling unit and the requester are asynchronous with each other, and it is not necessary for them to cooperate with each other. As compared with the technique described in Japanese Patent Application Laid-Open Publication No. 5-103324, therefore, a simple algorithm is implemented. Therefore, a circuit which is simpler and has a smaller circuit scale can be implemented.

Incidentally, as shown in FIG. 10, one requester 25 may issue the read requests of pixel value information for the plural output video image (i.e. the output video image 15(1) to 15(4)) to the RAM controller 23a. It is a point that the read requests of pixel value information for the plural output video image are issued to the RAM controller 23a.

In the present embodiment, an example in which four video signals are input and four composite video images are generated has been described. However, it is not necessary that the number of input video image signals is four. The number of the generated composite video images is not restricted to four, either. The number of the video signals and the number of the composite video images may be larger or smaller than four, so long as the number is at least two. The numbers may be different from each other. Furthermore, standards for the input video signals and the output video signals may not be ITU-R BT.656. In the present embodiment, the method of simply averaging pixel values is used as the downscaling processing. Since the downscaling algorithm itself has no relation to the essence of the present embodiment, a method using some filter may also be used. In the present embodiment, each of the RAM and the RAM controller is a single device. Alternatively, each of the RAM and the RAM controller may be divided into a plurality of elements according to the number of the variable downscaling units and the number of outputs (the number of the video layout information pieces). The present invention incorporates this case as well. The video layout may include deposing one or more of a plurality of input video images according to a layout pattern, and in addition, cutting off a part of the input video image to depose the cut off input video image. Further, the video layout may include superposing the input video images to dispose the superposed input video images. The video layout may include displaying background color in a region in which the video images are not disposed. The video layout may include displaying a frame on surroundings of the input video image. The video layout may include inversion of video images, or superposing a plurality of video images and conducting transparent composition. The processing conducted by the analysis units, the variable downscaling units, the video layout information manager, the requesters and the regenerators may be implemented by causing a computer to execute a program generated on the basis of an ordinary programming technique, or the processing may be implemented using hardware. Description described in the present paragraph is applied to embodiments described later as well in the same way.

Second Embodiment

Figure 4:
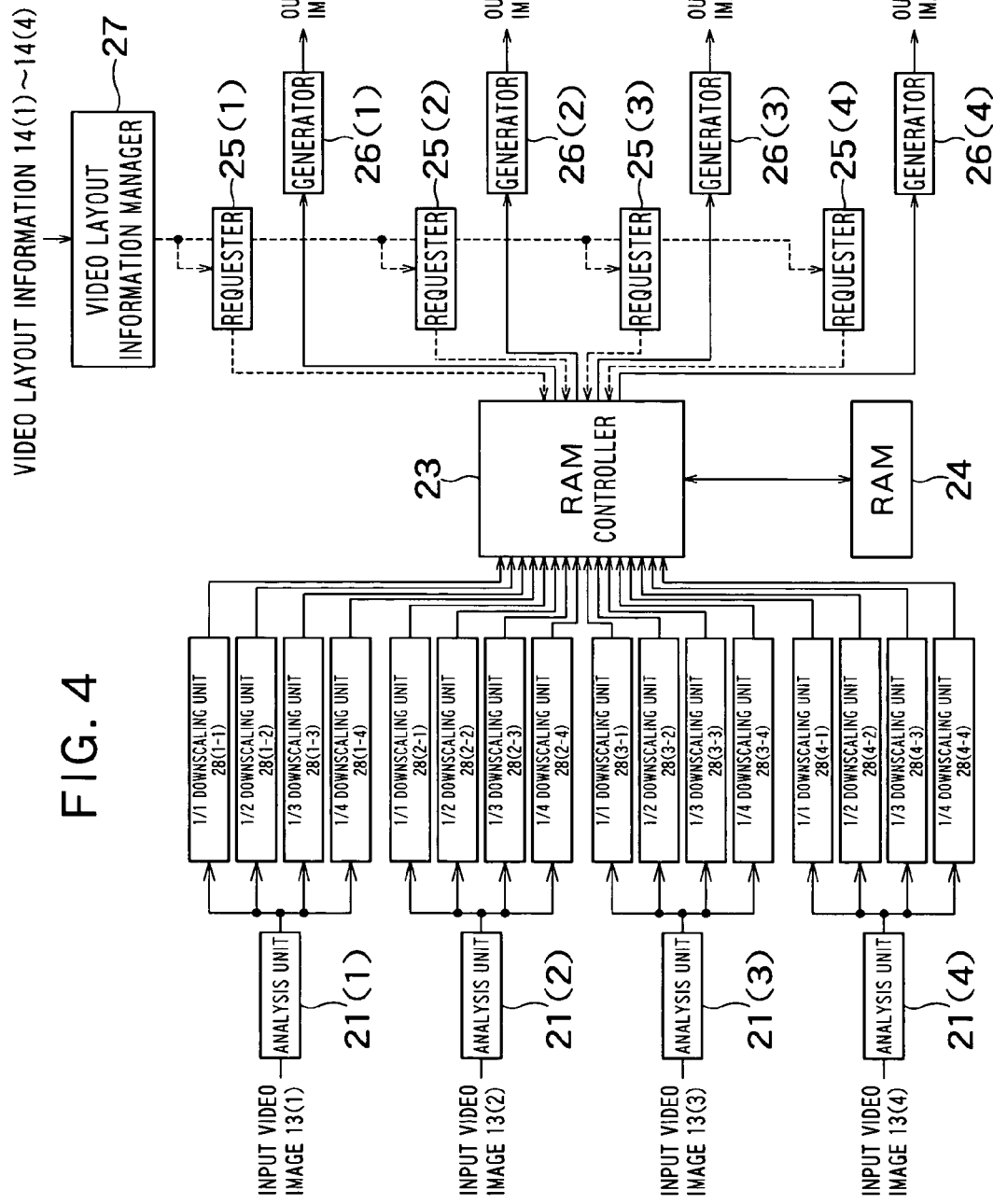
FIG. 4 is a block diagram schematically showing a configuration of a video composition apparatus according to a second embodiment of the present invention.

FIG. 4 is a block diagram schematically showing a configuration of a video composition apparatus according to a second embodiment of the present invention.

The present embodiment differs from the first embodiment in that the variable downscaling units 22(1-1) to 22(1-4), 22(2-1) to 22(2-4), 22(3-1) to 22(3-4) and 22(4-1) to 22(4-4) shown in FIG. 1 are replaced by fixed downscaling units 28(1-1) to 28(1-4), 28(2-1) to 28(2-4), 28(3-1) to 28(3-4) and 28(4-1) to 28(4-4) which conduct downscaling with fixed factors.

Each of the fixed downscaling units 28(1-1) to 28(1-4), 28(2-1) to 28(2-4), 28(3-1) to 28(3-4) and 28(4-1) to 28(4-4) conducts downscaling with only a definite downscaling factor, and a downscaling factor is not specified by the video layout information manager 27. Irrespective of the dynamically changing video layout information, each of the fixed downscaling units 28(1-1) to 28(1-4), 28(2-1) to 28(2-4), 28(3-1) to 28(3-4) and 28(4-1) to 28(4-4) downscales the input video image always with the same downscaling factor, and writes the pixel value information into the RAM 24 via the RAM controller 23. In the present example, four fixed factors 1/1, 1/2, 1/3 and 1/4 are given. A total of 4×4=16 frame buffers are present on the RAM 24. (In the case of the so-called double buffer, as many frame buffers as twice are present).

A configuration and operation of the remaining components are the same as those in the first embodiment.

In other words, the requesters 25(1) to 25(4) issue a read request of pixel value information from a frame buffer in the RAM 24, to the RAM controller 23 on the basis of the video layout information in the video layout information manager 27 and coordinate information specified by the generators 26(1) to 26(4). The RAM controller 23 reads out pixel value information from the RAM 24, and outputs the pixel value information to the generators 26(1) to 26(4). It is now supposed that, for example, the above-described video layout shown in FIG. 3 is used. If the coordinate value specified by the generator 26(1)-26(4) indicates an upper left-hand position in the video layout, the requester 25(1)-25(4) specifies a coordinate address in the input video image 13(1) downscaled to 1/2. If the coordinate value specified by the generator 26(1)-26(4) indicates an upper right-hand position in the video layout, the requester 25(1)-25(4) specifies a coordinate address in the input video image 13(2) downscaled to 1/2. If the coordinate value specified by the generator 26(1)-26(4) indicates a lower left-hand position in the video layout, the requester 25(1)-25(4) specifies a coordinate address in the input video image 13(3) downscaled to 1/2. If the coordinate value specified by the generator 26(1)-26(4) indicates a lower right-hand position in the video layout, the requester 25(1)-25(4) specifies a coordinate address in the input video image 13(4) downscaled to 1/2. The RAM controller 23 reads pixel value information from an address in the RAM 24 specified by the requester 25(1)-25(4), and delivers the pixel value information thus read to the generator 26(1)-26(4).

Effects of the present embodiment will now be described as compared with the first embodiment and the conventional techniques.

In the first and second embodiments, the number of input video images is four. It is now supposed that the number of input video images is N. In the second embodiment, four fixed downscaling units respectively having downscaling factors 1/1, 1/2, 1/3 and 1/4 are provided per input video image. The number of fixed downscaling may be greater than four or may be less than four so long as it is at least two. The number of fixed downscaling per input video image is denoted by M. However, the 1/1 downscaling unit does not conduct substantially downscaling processing. Therefore, the total number of the fixed downscaling units substantially becomes (M−1)×N. On the other hand, if the same N input video images and N output video images are implemented, N×N variable downscaling units become necessary according to Japanese Patent Application Laid-Open No. 5-103324 or the first embodiment. The ratio between them is (M−1)/N.

Taking the MCU in the realistic video conference and a screen split unit in a surveillance camera into consideration, the value of N is typically 4 or more in many cases. On the other hand, as for the value of M, the number of input video images arranged on a composite screen is at most approximately 4 in one direction (in other words, at most approximately 4×4=16 on the screen). Therefore, downscaling factors 1/1, 1/2, 1/3, 1/4, 2/3 and 3/4 (six in total downscaling factors) are often utilized. The number is at most approximately 5 except 1/1. If N≧4 and M=6, therefore, it follows that (M−1)/N≧5/4≈1. The number of fixed downscaling units is equal to at most the number of variable downscaling units.

Unlike the fixed downscaling units having fixed downscaling factors, the variable downscaling units having variable downscaling factors must cope with every possible downscaling factor. Therefore, the variable downscaling units becomes far greater in circuit scale than the fixed downscaling units. If (M−1) is approximately equal to N, therefore, the circuit scale of the downscaling units as a whole can be made far smaller according to the present embodiment as compared with the first embodiment and the conventional techniques.

Third Embodiment

Figure 5:
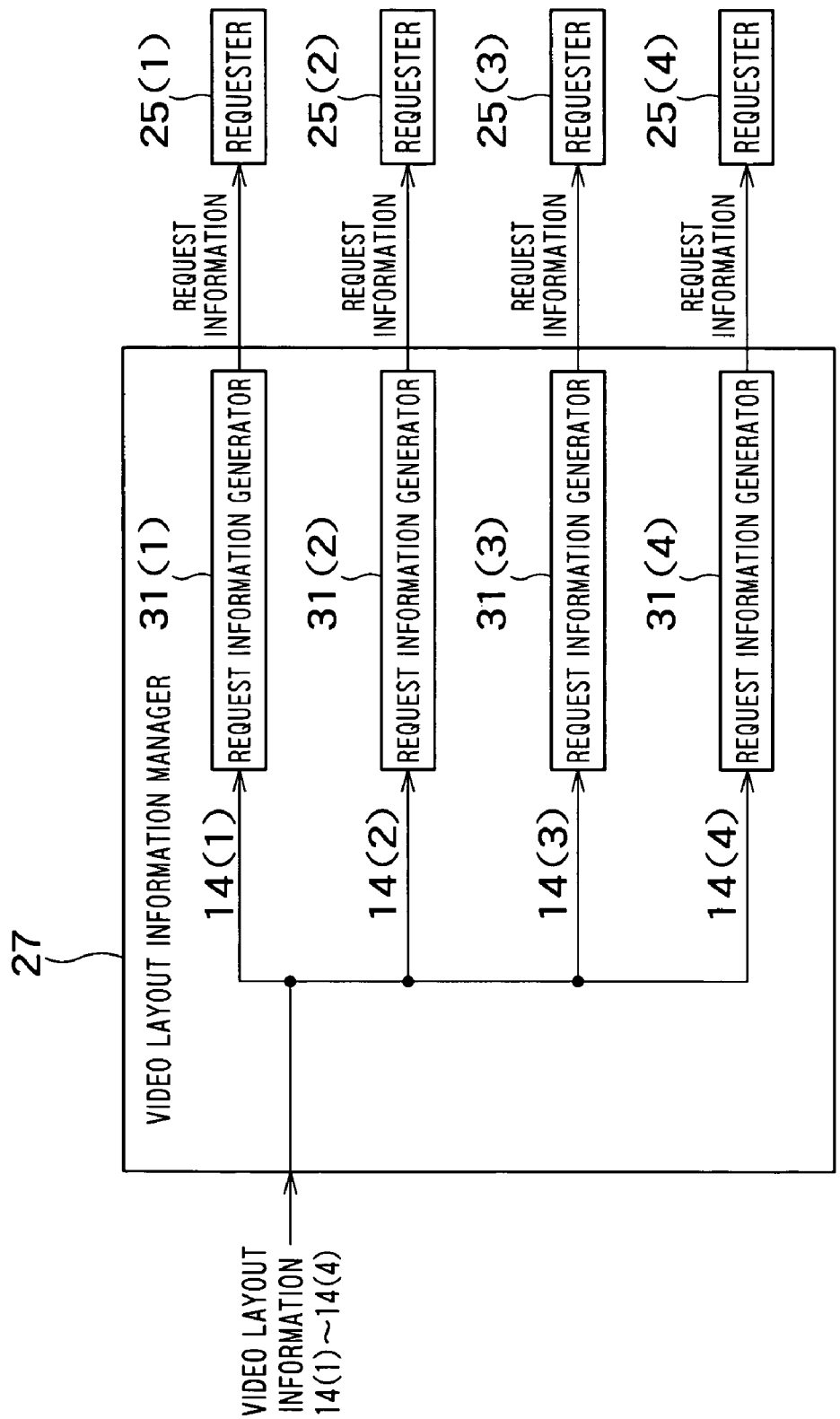
FIG. 5 is a diagram showing a configuration of a video layout information manager having a plurality of request information generators.

In the first and second embodiments, it has been described that the requesters shown in FIGS. 1 and 4 issue a read request to the RAM controller by using the video layout information. As a matter of fact, however, the requesters shown in FIGS. 1 and 4 issue a read request to the RAM controller 23 by using request information generated from video layout information. For the requesters to issue a read request, therefore, it is necessary to previously acquire the request information. This request information is generated by the video layout information manager 27. For example, as shown in FIG. 5, therefore, the video layout information manager 27 includes request information generators 31(1) to 31(4) which generate request information on the basis of video layout information 14(1) to 14(4).

The video layout information and the request information will now be described briefly.

The video layout information is information which prescribes arrangement of input video images. In general, it is natural that the information has a form, "a specified input video image is arranged in a position on an output video image." Specifically it is supposed that coordinates of an effective portion (portion obtained by excluding blanks) are X=0 to 720 and Y=0 to 480. In the case of the composite image shown in FIG. 3, a video image obtained by downscaling the input video image 13(1) to 1/2 is arranged in positions beginning with (0, 0), and a video image obtained by downscaling the input video image 13(2) to 1/2 is arranged in positions beginning with (360, 0). A video image obtained by downscaling the input video image 13(3) to 1/2 is arranged in positions beginning with (0, 240), and a video image obtained by downscaling the input video image 13(4) to 1/2 is arranged in positions beginning with (360, 240). By representing this as a set of subset information (input video number, x coordinate, y coordinate, scaling factor), (1, 0, 0, 1/2), (2, 360, 0, 1/2) and so on are obtained. By the way, the input video number 1 corresponds to the input video image 13(1), and the input video number 2 corresponds to the input video image 13(2).

On the other hand, the request information is used to determine by the requester contents of the request to the RAM controller 23 on the basis of current coordinates received from the generator. It is desirable that the request information has a form, "in a specified position on an output video image, an input video image is arranged." In other words, in positions beginning with (0, 0), a video image obtained by downscaling the input video image 13(1) to 1/2 is arranged. In positions beginning with (360, 0), a video image obtained by downscaling the input video image 13(2) to 1/2 is arranged. In positions beginning with (0, 240), a video image obtained by downscaling the input video image 13(3) to 1/2 is arranged. In positions beginning with (360, 240), a video image obtained by downscaling the input video image 13(4) to 1/2 is arranged. Upon obtaining this information, the requester can specify and obtain an input video image to be requested on the basis of the current coordinates. In more detail, the requester specifies an address on the RAM for a video image to be requested. Description concerning correspondence and translation processing to the address on the RAM will be omitted.

This layout example is a simple example. For example, there may also be the case where input video images are superposed so as to overlap each other. In that case as well, however, processing is conducted in the same way except that the request information generators analyzes the overlapping and in an overlapped region their highest layer input image becomes an placed video image. Furthermore, there is also the case where a region in which any video image is not disposed is present. In that case, a predetermined background color or a background video image is disposed in that region. In this case as well, the remaining processing is the same.

Before video frames are generated by the generators, i.e., before the requesters issue a read request to the RAM controller 23, it is necessary for the requesters to previously set the request information (or at least a part of the request information) therein. While the requesters 25(1) to 25(4) are not in operation, i.e., during, for example the vertical blank interval, the request information generators 31(1) to 31(4) shown in FIG. 5 generate request information on the basis of the video layout information 15(1) to 15(4). During this vertical blank interval, the requesters 25(1) to 25(4) receive request information required in the video frame of this time from the request information generators 31(1) to 31(4), and set it therein. It is repeated to generate request information in the blank interval over which the requesters 25(1) to 25(4) are not in operation and use the request information in the effective interval (non-blank interval) of a video frame.

Figure 7:
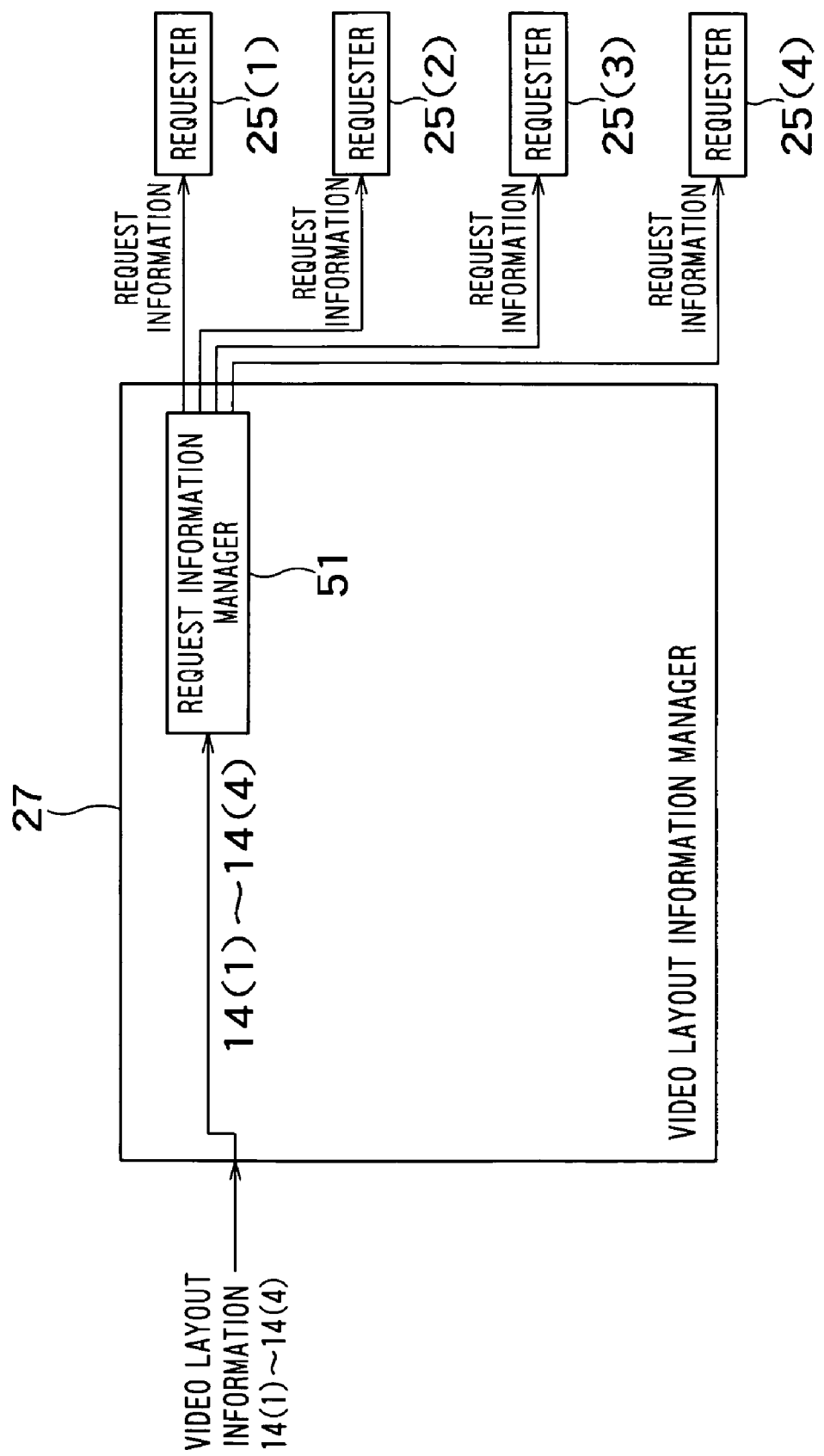
FIG. 7 is a diagram showing a configuration of a video layout information manager having a single request information generator.

In FIG. 5, a plurality of request information generators 31(1) to 31(4) are provided in the video layout information manager 27. Alternatively, the circuit scale can be further reduced by providing a single request information generator 51 in the video layout information manager 27 as shown in FIG. 7. The request information generator 51 generates request information pieces respectively for the requesters 25(1) to 25(4) in a time division manner. Hereafter, this will be described in detail.

Figure 6:
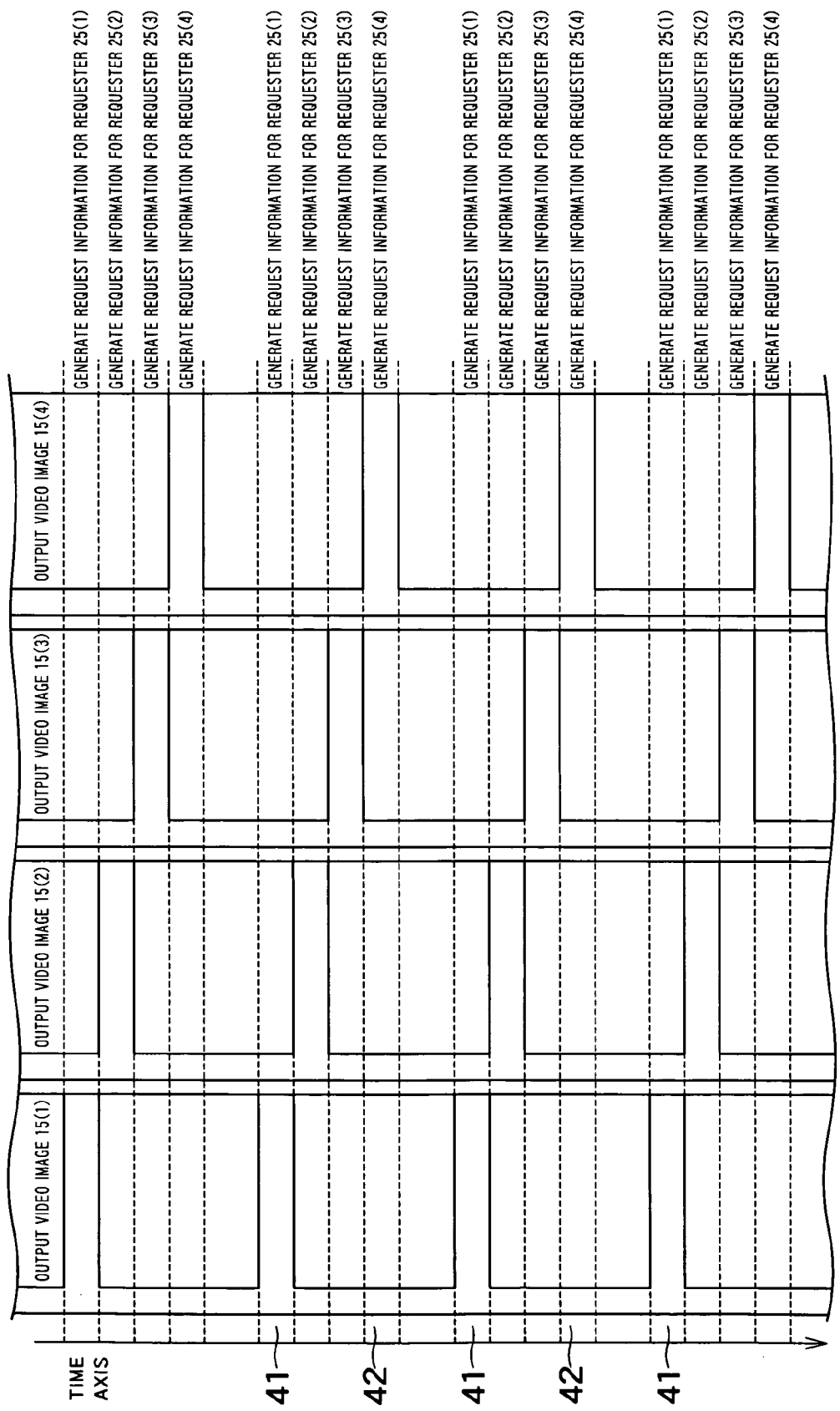
FIG. 6 is a diagram showing how a plurality of video frames are output along time.

FIG. 6 is a diagram showing how video frames are output from the generators 26(1) to 26(4) along the time axis.

Shaded regions represent vertical blanks 41 and horizontal blanks 42. Portions surrounded by the vertical blanks 41 and the horizontal blanks 42 are effective portions in video frames. The generators 26(1) to 26(4) are formed to generate Y coordinates with a time shift corresponding to the vertical blank. In other words, video frames are generated and output at timing which prevents vertical blank intervals of the generators 26(1) to 26(4) from overlapping each other.

By thus staggering the generation and output timing of video frames, time for generating request information on the requesters 25(1) to 25(4) can be staggered. As shown in FIG. 7, request information can be generated in a time division manner by using a single request information generator. However, it is supposed that time for generating one request information piece is shorter than the vertical blank interval.

In the present embodiment heretofore described, the generators generate video frames so as to cause vertical blank intervals not to overlap at all. However, this is an example. Portions may overlap each other. Therefore, the present invention is not restricted to the above-described contents. Furthermore, the request information generator may generate request information in an effective interval of video frames. What is essential is that generation and output timing of video frames can be staggered so as to cause the request information generator to be able to generate request information pieces to be used by a plurality of requesters, in a time division manner.

According to the present embodiment, the request information generator can be shared by a plurality of requesters as heretofore described. Further reduction of the circuit scale is possible.

Fourth Embodiment

In the first to third embodiments, the scaling factors are discrete in the case of the configuration having fixed downscaling units shown in FIG. 4. Even in the case of the variable downscaling units shown in FIG. 1, the scaling factors may become discrete considering the mounting cost. In the present embodiment, a mode in which these discrete scaling factors are complemented will now be described.

Figure 8:
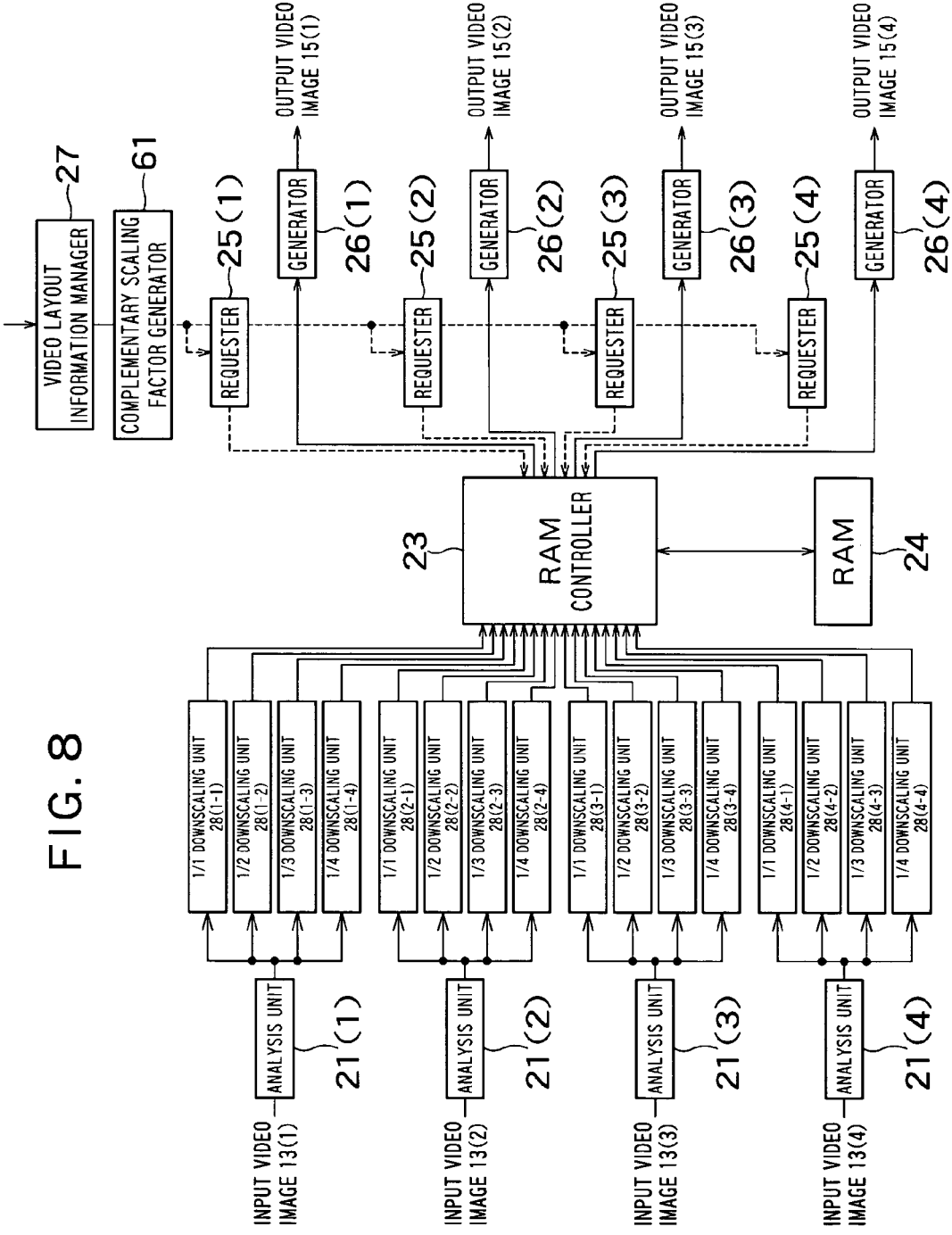
FIG. 8 is a block diagram schematically showing a configuration of a video composition apparatus according to a fourth embodiment of the present invention.

FIG. 8 is a block diagram schematically showing a configuration of a video composition apparatus according to a fourth embodiment of the present invention.

A complementary scaling factor generator 61 is disposed between the video layout information manager 27 and the requesters 25(1) to 25(4). The complementary scaling factor generator corresponds to, for example, a scaling factor division unit. In the present example, the fixed downscaling units shown in FIG. 4 are used as the downscaling units for input video images. However, the variable downscaling units shown in FIG. 1 may be used. The complementary scaling factor generator may be prepared for each output video image (for each generator). In the present example, however, the single complementary scaling factor generator 61 conducts processing for a plurality of output video images in a time division manner.

The complementary scaling factor generator 61 conducts scaling factor division processing that represents a scaling factor calculated by the video layout information manager 27 as a product of a partial scaling factor that can be executed by the downscaling unit and a complementary scaling factor.

Supposing that, for example, information indicating 1/2.5 downscaling of the input video image 13(1) is given from the video layout information manager 27, 1/2.5 can be represented 1/2.5=1/2×4/5. Therefore, the complementary scaling factor generator 61 generates 4/5 as the complementary scaling factor. And the complementary scaling factor generator 61 gives request information to, for example, the requester 25(1) to request the requester 25(1) to thin out 1/2-downscaled image of the input video image 13(1) according to a ratio of 4/5 and use a resultant video image. As a result, a video image downscaled to 1/2.5 is output to the generator 26(1). Or 1/2.5 can be represented as 1/2.5=1/3×6/5. Therefore, the complementary scaling factor generator 61 may generate a complementary scaling factor 6/5 and give request information to the requester 25(1) to request the requester 25(1) to utilize 1/3-downscaled video images 13(1) in part redundantly and use a resultant image so as to upscale the 1/3-downscaled video images 13(1) to 6/5 times.

According to the present embodiment, it becomes possible to implement a continuous scaling factor for the input video image while keeping the size of the downscaling units small.

Fifth Embodiment

In the present embodiment, another model in which the discrete downscaling factor is complemented will be described.

FIG. 9 is a block diagram schematically showing a configuration of a video composition apparatus according to a fifth embodiment of the present invention. FIG. 9 differs from FIG. 8 in that scaling units 71(1) to 71(4) are disposed between the RAM controller 23 and the generators 26(1) to 26(4) to conduct complementary upscaling or downscaling on video images. The scaling units correspond to video complementary scaling units, video complementary downscaling units, or video complementary upscaling units.

Supposing that, for example, information indicating 1/2.5 downscaling of the input video image 13(1) is given from the video layout information manager 27, 1/2.5 can be represented as 1/2.5=1/2×4/5. Therefore, the complementary scaling factor generator 61 generates 4/5 as the complementary scaling factor. And the complementary scaling factor generator 61 gives request information to, for example, the requester 25(1) to downscale the input video image 13(1) at a ratio of 1/2, and orders the scaling unit 71(1) to conduct 4/5 downscaling. As a result, a video image downscaled to 1/2.5 is output to the generator 26(1). Or 1/2.5 can be represented as 1/2.5=1/3×6/5. Therefore, the complementary scaling factor generator 61 may generate 6/5 as the complementary scaling factor and order the scaling units 71(1) to 71(4) to conduct 6/5 upscaling.

As appreciated from the first to fourth embodiments, one of great features in the embodiments of the present invention is that downscaling processing and composition processing are separated from each other to facilitate processing by disposing downscaling units in a stage preceding the RAM controller to downscale input video images and disposing the requesters and the generators in a stage subsequent to the RAM controller to conduct the composition processing. Viewing from this point, the present fifth embodiment appears to be contrary to this feature. However, the scaling units in the present embodiment are provided to complement the discrete downscaling factors of the downscaling units. Therefore, the scaling factors in the scaling units are close to unity and their variation widths are also small. Accordingly, variation of the processing delay caused by variation of the scaling factor in each of the scaling units is small. Therefore, the delay can be easily estimated. As a result, reduction of the circuit scale obtained by simplifying the processing, which is one of the effects according to the embodiments of the present invention, is not hampered.

It is also possible to combine the fifth embodiment heretofore described with the fourth embodiment.

In other words, the complementary scaling factor generator represents the scaling factor of an input image as a product of a partial scaling factor that can be implemented by the downscaling unit and the complementary scaling factor.

Thereafter, if the complementary scaling factor is, for example, greater than unity, the scaling unit upscales the input video image read out from the RAM controller, with the complementary scaling factor. If the complementary scaling factor is less than unity, the requester requests the RAM controller to read out the input video image thinned out according to the complementary scaling factor.

Or if the complementary scaling factor is less than unity, the scaling unit downscales the input video image read out from the RAM controller with the complementary scaling factor. If the complementary scaling factor is greater than unity, the requester requests the RAM controller to read out the input video image in part redundantly according to the complementary scaling factor and use a resultant video image.

In the embodiments, the video conference server is shown as heretofore described. However, the present invention concerns the general composition processing for inputting a plurality of video images and outputting a plurality of composite video images. The present invention is not restricted to the video conference server. For example, the present invention may be used in an application which a plurality of surveillance camera images are input and composed for the purpose of surveillance. Or the present invention may be used in an application which composes a PC screen, a TV screen, a game screen or the like in offices and homes. In this way, the present invention may be used in any application. The use application of the apparatus is not restricted. The classification/signal format of input and output video images are not restricted (they may be different in channels).

What is claimed is:

1. A video composition apparatus comprising:
   I video scaling units each of which is configured to scale an input video image with scaling factors to generate scaled input video images;
   a video storage unit configured to store the scaled input video images;
   write requesters, provided so as to be respectively associated with the video scaling units, each of which is configured to generate a write request to request the video storage unit to write the scaled input video images generated by the video scaling units into predetermined regions in the video storage unit;
   one or more read requesters configured to issue read requests of scaled input video images in the video storage unit on the basis of each of J video layout information pieces each of which prescribes layout of the scaled input video images for one of a plurality of composite video images;
   a read controller configured to read out scaled input video images from the video storage unit in response to the read requests;
   J composite video image generators, provided so as to be respectively associated with the J video layout information pieces, each of which is configured to generate one of the composite video images from the scaled video images read out by the read controller correspondingly to one of the video layout information pieces; and
   a scale designation unit configured to designate a plurality of scaling factors on the basis of the video layout information pieces to each of the video scaling units, wherein
   each video scaling unit is configured to scale the input video image according to the scaling factors supplied by the scale designation unit to generate scaled input video images,
   the scale designation unit designates J scaling factors as the plurality of scaling factors, to each of the video scaling units, and
   each video scaling unit includes J scaling units each of which scales the input video image according to a different one of the J scaling factors designated by the scale designation unit.

2. The video composition apparatus according to claim 1, wherein each of the video scaling units downscales the input video image with downscaling factors to generate downscaled input video images.

3. The video composition apparatus according to claim 1, further comprising:
   a scaling factor division unit configured to divide each of the scaling factors as a product of a partial scaling factor that can be executed by the video scaling units and a complementary scaling factor; and wherein
   if the complementary scaling factor is less than unity, the scaling factor division unit requests the read requester to thin out scaled input video images according to the complementary scaling factor, and
   if the complementary scaling factor is greater than unity, the scaling factor division unit requests the read requester to utilize scaled input video images in part redundantly according to the complementary scaling factor.

4. The video composition apparatus according to claim 1, further comprising:
   a scaling factor division unit configured to divide each of the scaling factors as a product of a partial scaling factor that can be executed by the video scaling units and a complementary downscaling factor having a value less than unity; and wherein the scaling factor division unit requests the read requester to thin out scaled input video images according to the complementary downscaling factor.

5. The video composition apparatus according to claim 1, further comprising:

a scaling factor division unit configured to divide each of the scaling factors as a product of a partial scaling factor that can be executed by the video scaling units and a complementary upscaling factor having a value greater than unity and wherein the scaling factor division unit requests the read requester to utilize scaled input video images in part redundantly according to the complementary scaling factor.

6. The video composition apparatus according to claim 1, further comprising:

a scaling factor division unit configured to divide each of the scaling factors as a product of a partial scaling factor that can be executed by the video scaling units and a complementary scaling factor; and video complementary scaling units each of which is configured to scale scaled input video images read out from the read controller according to the complementary scaling factor and output resultant video images to one of the composite video image generators; and wherein the video complementary scaling units are provided so as to be respectively associated with the composite video image generators.

7. The video composition apparatus according to claim 1, further comprising:

a scaling factor division unit configured to divide each of the scaling factors as a product of a partial scaling factor that can be executed by the video scaling units and a complementary downscaling factor having a value less than unity; and video complementary downscaling units each of which is configured to downscale scaled input video images read out from the read controller according to the complementary downscaling factor and output resultant video images to one of the composite video image generators; and wherein the video complementary downscaling units are provided so as to be respectively associated with the composite video image generators.

8. The video composition apparatus according to claim 1, further comprising a scaling factor division unit configured to divide each of the scaling factors as a product of a partial scaling factor that can be executed by the video scaling units and a complementary upscaling factor having a value greater than unity; and video complementary upscaling units each of which is configured to upscale scaled input video images read out from the read controller according to the complementary upscaling factor and output resultant video images to one of the composite video image generators; and wherein the video complementary upscaling units are provided so as to be respectively associated with the composite video image generators.

9. The video composition apparatus according to claim 1, further comprising:

a scaling factor division unit configured to divide each of the scaling factors as a product of a partial scaling factor that can be executed by the video scaling units and a complementary scaling factor; and video complementary upscaling units each of which is configured to upscale scaled input video images read out from the read controller according to the complementary scaling factor and output resultant video images to one of the composite video image generators, when the complementary scaling factor is greater than unity; and wherein the video complementary upscaling units are provided so as to be respectively associated with the composite video image generators, and when the complementary scaling factor is less than unity, the scaling factor division unit requests the read requester to thin out scaled input video images according to the complementary scaling factor.

10. The video composition apparatus according to claim 1, further comprising:

a scaling factor division unit configured to divide each of the scaling factors as a product of a partial scaling factor that can be executed by the video scaling units and a complementary scaling factor; and video complementary downscaling units each of which is configured to downscale scaled input video images read out from the read controller according to the complementary scaling factor and output resultant video images to one of the composite video image generators, when the complementary scaling factor is less than unity; and wherein the video complementary downscaling units are provided so as to be respectively associated with the composite video image generators, and when the complementary scaling factor is greater than unity, the scaling factor division unit requests the read requester to utilize scaled input video images in part redundantly according to the complementary scaling factor.

11. A video composition apparatus comprising:

I video scaling units each of which is configured to scale an input video image with scaling factors to generate scaled input video images;

a video storage unit configured to store the scaled input video images;

write requesters, provided so as to be respectively associated with the video scaling units, each of which is configured to generate a write request to request the video storage unit to write the scaled input video images generated by the video scaling units into predetermined regions in the video storage unit;

one or more read requesters configured to issue read requests of scaled input video images in the video storage unit on the basis of each of J video layout information pieces each of which prescribes layout of the scaled input video images for one of a plurality of composite video images;

a read controller configured to read out scaled input video images from the video storage unit in response to the read requests;

J composite video image generators, provided so as to be respectively associated with the J video layout information pieces, each of which is configured to generate one of the composite video images from the scaled video images read out by the read controller correspondingly to one of the video layout information pieces, wherein each video scaling unit includes a plurality of fixed scaling units respectively having fixed scaling factors different from each other.

12. The video composition apparatus according to claim 11, wherein each video scaling unit includes as many fixed scaling units as the number of scaling factors that can be specified by the video layout information pieces.

13. A video composition apparatus comprising:

I video scaling units each of which is configured to scale an input video image with scaling factors to generate scaled input video images;

a video storage unit configured to store the scaled input video images;

write requesters, provided so as to be respectively associated with the video scaling units, each of which is configured to generate a write request to request the video storage unit to write the scaled input video images generated by the video scaling units into predetermined regions in the video storage unit;

one or more read requesters configured to issue read requests of scaled input video images in the video storage unit on the basis of each of J video layout information pieces each of which prescribes layout of the scaled input video images for one of a plurality of composite video images;

a read controller configured to read out scaled input video images from the video storage unit in response to the read requests;

J composite video image generators, provided so as to be respectively associated with the J video layout information pieces, each of which is configured to generate one of the composite video images from the scaled video images read out by the read controller correspondingly to one of the video layout information pieces; and a request information generator configured to generate request information which is coordinate information of input video images to be disposed on respective coordinate regions on a composite video image, wherein the read requester starts the issue of the read requests so as to cause staggering by a time required to generate the request information at least in accordance with an order by which request information is generated.

14. The video composition apparatus according to claim 13, wherein the request information generator completes generating the request information within a vertical blanking interval of the composite video image associated with each of the video layout information pieces.

15. A video composition method comprising:

scaling each of I input video images with scaling factors to generate a plurality of scaled input video images each corresponding to one of the input video images;

writing the scaled input video images into predetermined regions in a video storage unit;

reading out video image signals from the video storage unit on the basis of each of J video layout information pieces, each of which prescribes layout of the scaled input video images for one of a plurality of composite video images;

generating the composite video images from the video image signals read out from the video storage unit for every video layout information piece;

transmitting the composite video images generated for every video layout information piece to a corresponding one of a plurality of terminals via a network for display at the terminals; and designating a plurality of scaling factors on the basis of the video layout information pieces for each of the I input video images, wherein the scaling of each of I input video images includes scaling each of the input video images according to the scaling factors designated for each of the I input video images to generate the scaled input video images, the designating includes designating J scaling factors as the plurality of scaling factors for each of the I input video images, and the scaling of each of I input video images includes scaling each of the input video images according to the J scaling factors designated for each of the I input video images.

16. A non-transitory program storage medium storing a computer program for inducing a computer to perform steps comprising:

scaling each of I input video images with scaling factors to generate a plurality of scaled input video images each corresponding to one of the input video images;

writing the scaled input video images into predetermined regions in a video storage unit;

reading out video image signals from the video storage unit on the basis of each of J video layout information pieces, each of which prescribes layout of the scaled input video images for one of a plurality of composite video images;

generating the composite video images from the video image signals read out from the video storage unit for every video layout information piece; and designating a plurality of scaling factors on the basis of the video layout information pieces for each of the I input video images, wherein the scaling of each of I input video images includes scaling each of the input video images according to the scaling factors designated for each of the I input video images to generate the scaled input video images, the designating includes designating J scaling factors as the plurality of scaling factors for each of the I input video images, and the scaling of each of I input video images includes scaling each of the input video images according to the J scaling factors designated for each of the I input video images.

17. A video apparatus comprising:

video scaling units, each of which scales an input video image supplied thereto to generate a scaled video image;

a video storage unit for storing scaled video images;

at least one read requester for issuing read requests for scaled video images to the video storage unit in accordance with J video layout information pieces, each video layout information piece specifying a layout of scaled video images for one of a plurality of composite video images;

a read controller for reading out scaled video images from the video storage unit in response to the read requests;

J composite video image generators, each of which generates a respective one of the composite video images based on the read out scaled video images; and a scale designation unit configured to designate a plurality of scaling factors on the basis of the video layout information pieces to each of the video scaling units, wherein each video scaling unit is configured to scale the input video image according to the scaling factors supplied by the scale designation unit to generate scaled video images, the scale designation unit designates J scaling factors as the plurality of scaling factors, to each of the video scaling units, and each video scaling unit includes J scaling units each of which scales the input video image according to a different one of the J scaling factors designated by the scale designation unit.

* * * * *